United States Patent

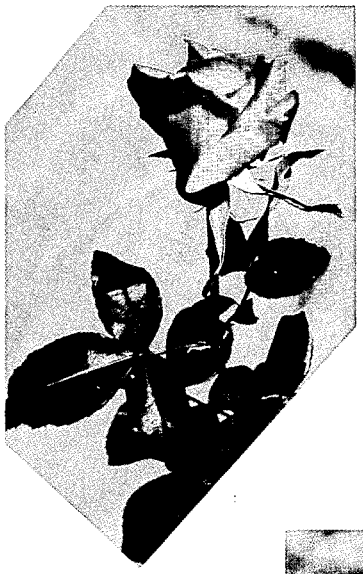
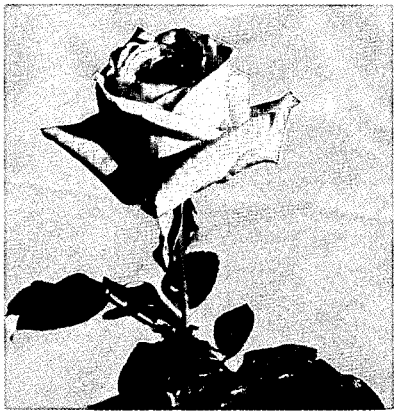
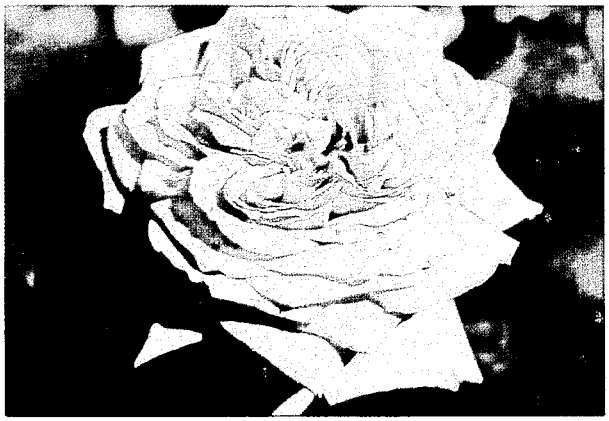
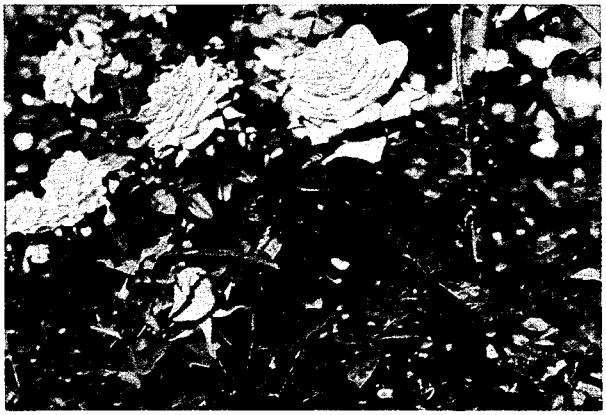

Plant Pat. 3,899
Patented June 1, 1976

3,899
ROSE PLANT

R. Merrell Graham, 507 Olustee Ave.,
Lake City, Fla. 32055

Filed Dec. 30, 1974, Ser. No. 537,997
Int. Cl. A01h *5/00*
U.S. Cl. Plt.—20 1 Claim

ABSTRACT OF THE DISCLOSURE

A rose plant of the hybrid tea class produced by crossing the variety of rose commonly referred to as Scarlet Knight with a second variety of rose commonly referred to as Charlotte Armstrong.

SUMMARY OF THE INVENTION

The present invention relates to a new and distinct variety of rose plant of the hybrid tea class which was originated by my crossing the variety Charlotte Armstrong with the variety Scarlet Knight.

The primary objective of this breeding was to produce a new rose plant of the hybrid tea class which would exhibit improved characteristics in its growth and uniqueness in its bloom. As a result of this breeding, I have produced a new and improved plant of the rose variety which is distinguishable from other roses of which I am aware as is evidenced by the following characteristics:

(1) Continually produce abundant blooms during the growing season even if plants are not groomed.
(2) Ease of reproduction by budding.
(3) A vigorous, upright manner of growth.
(4) Distinctively full bloom of medium size and of a rich red color.
(5) Abundant foliage covers the plant well.

Asexual reproduction of my new variety of hybrid tea demonstrates that the previously mentioned characteristics are established and transmitted through succeeding propagations.

BRIEF DESCRIPTION OF THE DRAWING

The accompanying drawing shows the vegetative growth and flowers of a typical specimen of the new variety of hybrid tea at several stages of the bloom development and is depicted in color as nearly true as is possible in such a reproduction.

DETAILED DESCRIPTION OF THE DISCLOSURE

The following is a detailed description of the new rose plant of hybrid tea class with the color terms being given in accordance with the color designations of the Royal Horticultural Society, R.H.S. Colour Chart, 1966.

Parentage:
- *Seed parent.*—Charlotte Armstrong.
- *Pollen parent.*—Scarlet Knight.

Classification:
- *Botanic.*—Rosa hybrid.
- *Commercial.*—Hybrid tea. Flower. Observations were made at Hattiesburg, Miss.

Blooming habit:
- *Blooms.*—Profusely.
- *Recurrent.*—Continuous.

Bud:
- *Size.*—Medium.
- *Form.*—Pointed.

- *Color.*—When sepals first divide—color 59B. When petals begin to unfold—color 53B. When grown—inside and outside petal colors 53A and 53B respectively.
- *Sepals.*—Smooth on upper side with hairs on reverse side. Sepals curl back just before petals begin to unfold.
- *Calyx.*—Shape: Pear shape. Size: Large extending to ½ inch above bud. Aspect: Smooth with hairs on edge of each sepal. Odor: Some odor when rubbed.
- *Peduncle.*—Length: Medium, 2½ to 3 inches. Aspect: Prickly. Color: 143C, however, some variation dependent upon the stage of flower development. Strength: Erect. Opening: Buds open well and remain hardy.

Bloom:
- *Size.*—Medium-average size when fully expanded 4 inches.
- *Borne.*—Singly.
- *Stem.*—Medium-normal strength.
- *Form.*—When first open: High center. Permanent: Petals curl back, outer petals quilled and center of open flower somewhat confused.
- *Petalage.*—Very double 60 to 70.
- *Color.*—1st day—53B inside of petals; 53A reverse of petals. 2nd day—57A inside; 53C reverse. 3rd day—57B inside; 53D reverse. 4th day—57B inside; 57C reverse. 5th day—57B inside; 57C reverse. 6th day—57C inside; 57D reverse. 7th day—57C inside; 57C reverse.
- *Variegation.*—None.

Petals:
- *Texture.*—Leathery.
- *Appearance.*—Outside: Shiny. Inside: Velvety.
- *Form.*—Round.
- *Arrangement.*—Imbricated. Petals in center: Many.
- *Persistence.*—Drop off cleanly.
- *Fragrance.*—Moderate-average hybrid tea scent.
- *Lastingness.*—On plant: Very long. As cut flower: Very long.

Sexual organs:
- *Stamen anthers.*—Medium, many, color 15A along edges where they split and 66C on the underside of the stamen, arranged around styles mixed with petals.
- *Stamen filaments.*—Short, color 42C.
- *Pollen.*—Color 15B, very little.
- *Styles.*—Loosely separated, uneven lengths, medium length, thin.
- *Stigma.*—Color 8D.
- *Ovaries.*—Somewhat protruding from calyx. Plant.

Form: Bush.

Growth: Very vigorous, upright.

Foliage: 5 to 7 leaflets.
- *Size.*—Medium.
- *Quantity.*—Abundant.
- *Color.*—New foliage: 187A upper side, 187A underside. Old foliage: Upper side 137B, underside 138C.
- *Shape.*—Leaflets elliptic.
- *Texture.*—Upper side leathery. Under side smooth.
- *Ribs and veins.*—Prominent.
- *Edge.*—Serrated.
- *Serration.*—Single small.
- *Leaf stem.*—Color 138B, no special markings. Underside prickles.
- *Stipules.*—Medium bearded.

*Disease resistant.*—Slightly resistant to mildew and black spot.

Wood:

*New wood.*—Color 143B, bark smooth.

*Old wood.*—Color 138B with smooth bark.

Thorns:

*Thorns.*—Average quantity on main stem and lateral stems.

*Form.*—Broad base, medium length straight upward.

*Color when young.*—176A.

*Position.*—Irregular.

*Prickles.*—Quantity. On main stem: Few to many. On laterals: Few to many.

I claim:

1. A new and distinct variety of rose plant of the hybrid tea class, substantially as described and shown herein, characterized particularly by its continuous blooming during the growing season and its abundance of unique blooms having petals which curl back at maturity with the outer petals quilled and the center petals generally randomly oriented.

No references cited.

ROBERT E. BAGWILL, Primary Examiner